July 13, 1954 W. S. HAHN Plant Pat. 1,290
IVY PLANT
Filed Aug. 11, 1953
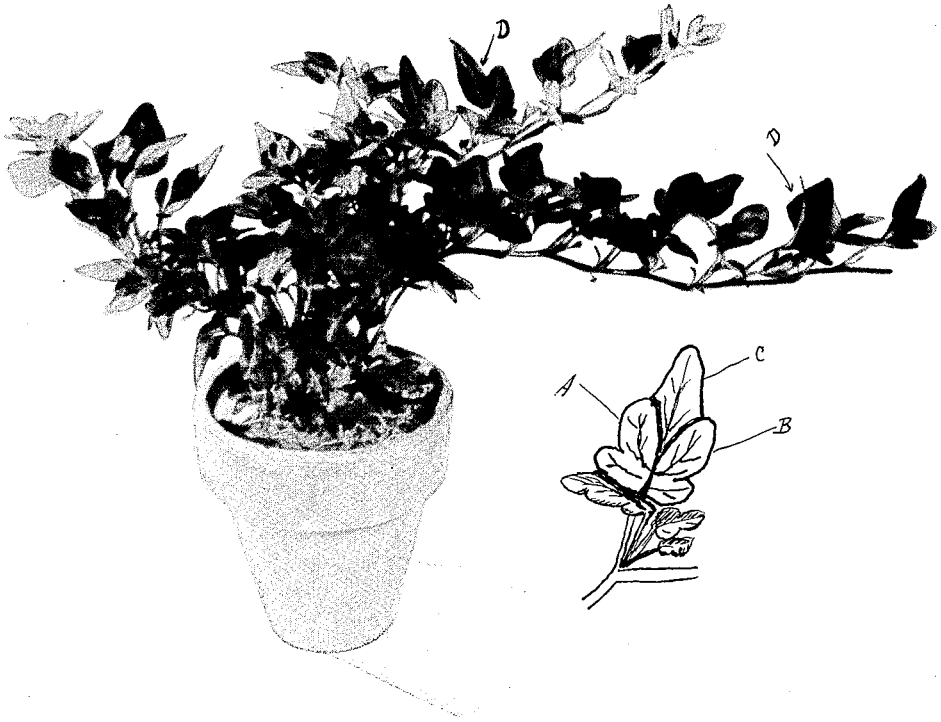
INVENTOR
Walter S. Hahn
By Orville M Kile
Plant patent agt.

Patented July 13, 1954

Plant Pat. 1,290

UNITED STATES PATENT OFFICE 1,290

IVY PLANT

Walter S. Hahn, Pittsburgh, Pa.

Application August 11, 1953, Serial No. 373,702

1 Claim. (Cl. 47—59)

My present discovery pertains to a new and useful variety of Hedra-helix suitable particularly for potted ornamental use and having readily distinguishable features of growth, especially its unique lobed or folded-over leaves more specifically described below.

This new variety is a sport or mutation of Hahn's Maple Queen, subject of United States Plant Patent No. 429. It was discovered by me in an extensive collection of ivies grown in greenhouses of which I am co-owner, in the suburbs of Pittsburgh, Pennsylvania, where I maintain vigilant watch for new and promising varities of Hedra-helix. This new variety has been reproduced asexually by me from cuttings, in these greenhouses near Pittsburgh and I have amply demonstrated over a period of several years that it reproduces true to type.

The accompanying color photographic illustration shows in four-fifth true size (in the original) and as nearly true colors as the color photographer could make it, a potted plant of this new variety at the age of about five months. The end of one of the branches has been clipped so as to fit within the space available. The black-and-white small diagrammatic illustration shows (slightly enlarged) the shape and form of a single mature leaf, and accompanying leaflets, which constitute the most unique features of the new variety. While the leaf shapes and arrangement on the stem as well as the coloration are typical for a five-month-old plant, it must be understood that there will be some variations as between individual specimens of the variety.

In the following detailed description of this new variety, ordinary dictionary terms are used except where color plates are cited. Such plate references are to Ridgway's Color Standards and Nomenclature.

Growth: Like other Hahn self-branching ivies, this new variety makes a compact and rapid growth. The short inter-nodes and multiple leaves or leaflets from each node give the plant an appearance of density and profusion of foliage, very desirable in a small potted plant.

Leaves:

*Shape.*—Notably different from other self-branching varieties, in that the leaves of this new variety are completely (or in some cases almost completely) dissected into three separate lobes. The two basal lobes, such as A and B on the diagram, have sinuses extending to the midrib and to a junction on the leaf blade slightly above the petiole. The basal portion of the terminal lobe, marked C, disappears underneath the two basal lobes, A and B, which must be turned back to disclose fully that there are in fact three separate lobes. Such disclosure may be seen in the photograph at the points marked D.

From the moment the leaf emerges from the bud stage the two basal lobes position themselves over-top of the terminal lobe and with the apex of the leaflets pointing in the same general direction as the apex of the terminal lobe.

This folding-over or over-topping effect of the two basal lobes in relation to the terminal lobe gives a general shape to the leaf entirely different from anything known to me in ivies. The apparent effect is as though the terminal lobe was winged, the two basal lobes forming the wings. The two basal lobes of the leaf are themselves indented or lobed, varying from a slight or moderate indentation to one-half the distance from margin to midrib. This secondary lobing also produces an interesting and unusual leaf appearance.

The leaf when viewed as a whole from above has a narrowed lanceolate shape, rounded at the apex, usually cordate at the base. The central or terminal lobe also is lanceolate in shape, rounded at the apex, and with a cuneate base. The two basal lobes are roughly lanceolate with apexes more rounded and bases odd-cuneate due to dissection.

*Position.*—The principal petioles and leaves emerge one from each node, but much smaller leaflets also emerge from the axil between the main petiole and the main stem. Although these leaflets remain comparatively small they give the effect of dense foliage and well-covered stems.

*Size.*—On young plants, leaf-blades average about one and one-half inches in length and from one-half to one inch broad.

*Substance.*—Substantial, with raised and prominent veins.

*Color.*—Leaves are a dark, lustrous green above—a little darker than Forest Green (Pl. XVII)—and a lighter green beneath, approximately Bice Green (Pl. XVII). The new growth at tips of branches is considerably lighter green, approaching Yellow Green (Pl. VI).

Having thus disclosed my discovery, I claim:

The new and distinct variety of ivy (Hedra-helix) plant of the self-branching type, substantially as herein shown and described, characterized particularly by its plentiful, dark-green, lanceolate-shaped leaves having deeply dissected lobes arranged and super-imposed in such a way as to give a winged effect.

No references cited.